United States Patent [19]

Hirschfeld

[11] B  3,999,855
[45] Dec. 28, 1976

[54] ILLUMINATION SYSTEM

[75] Inventor: Tomas Hirschfeld, Framingham, Mass.

[73] Assignee: Block Engineering, Inc., Cambridge, Mass.

[22] Filed: Oct. 24, 1974

[21] Appl. No.: 517,504

[44] Published under the second Trial Voluntary Protest Program on March 9, 1976 as document No. B 517,504.

[52] U.S. Cl. .............................. 356/103; 250/574
[51] Int. Cl.$^2$ ...................................... G01N 21/26
[58] Field of Search .......... 356/102, 103, 104, 208; 250/574, 575, 576

[56] References Cited

UNITED STATES PATENTS

| | | | |
|---|---|---|---|
| 3,506,360 | 4/1970 | Albert | 250/574 |
| 3,700,330 | 10/1972 | Davis | 356/102 |
| 3,850,525 | 11/1974 | Kaye | 356/103 |

*Primary Examiner*—Archie R. Borchelt
*Assistant Examiner*—D. C. Nelms
*Attorney, Agent, or Firm*—Schiller & Pandiscio

[57] ABSTRACT

An improved system is described for providing approximately equalized illumination at all points between first and second opposite portions of a total internally reflecting cell. The system comprises in addition to the cell, a source of radiation of at least one selected wavelength, means for directing the radiation along a plurality of paths, and means for introducing the radiation in at least two of the paths into first and second opposite portions of the cell. Means can be provided for varying the penetration angle of the radiation into the cell.

14 Claims, 6 Drawing Figures

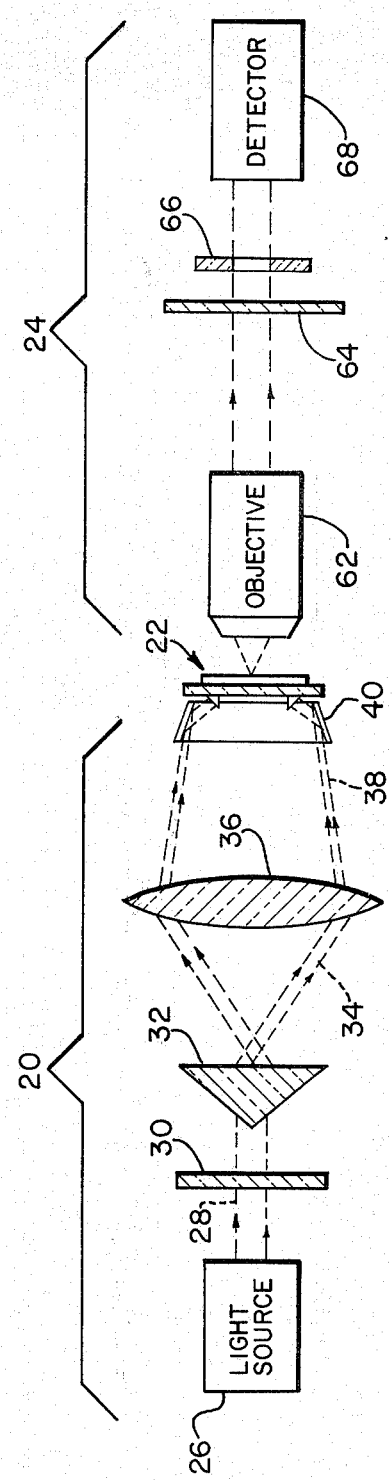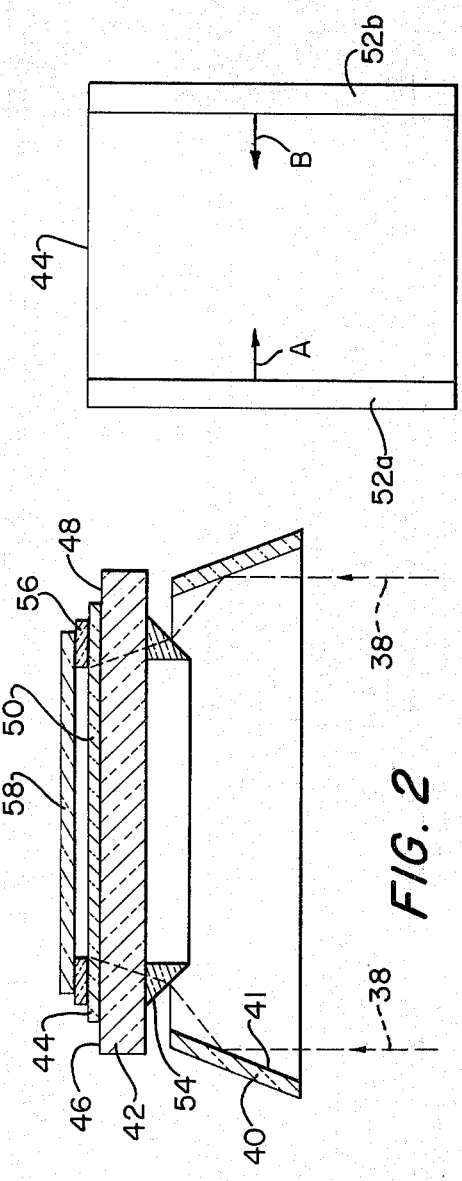

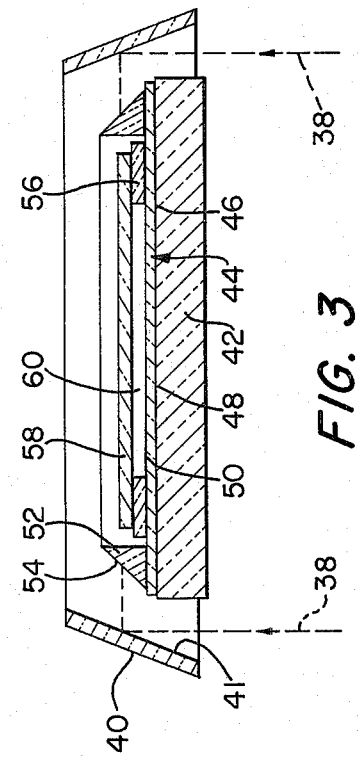
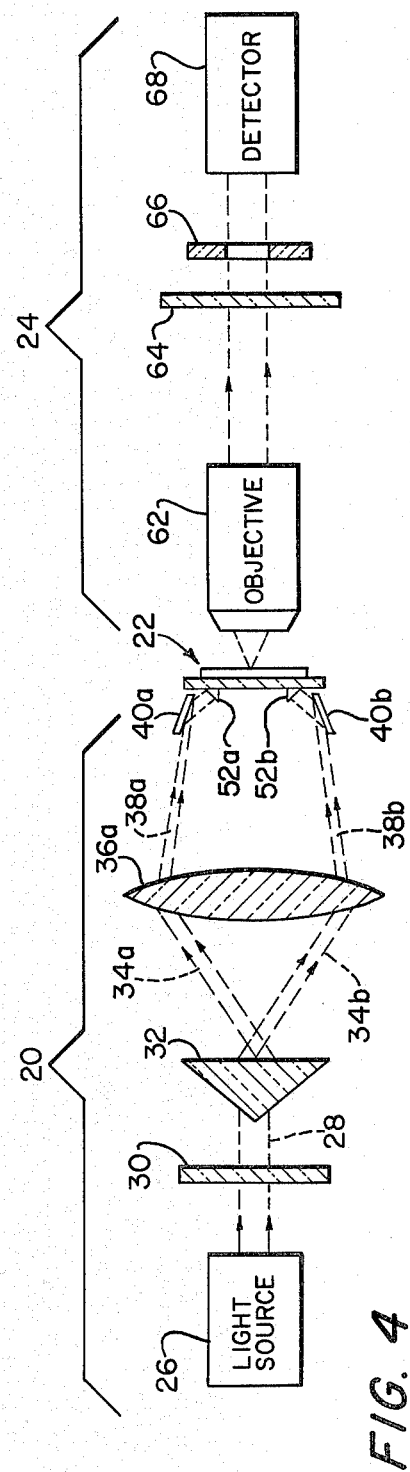
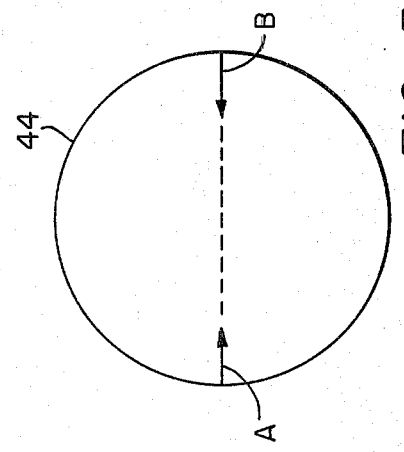

ILLUMINATION SYSTEM

This invention relates to optical systems and more particularly to the detection and classification of submicron-dimensioned particles, such as viruses in a fluid medium.

The detection and classification of submicron-dimensioned particles, particularly viruses, has long been an important goal frustrated by a number of vexing problems. One technique, however, which is promising, is described in copending application Ser. No. 498,382, filed Aug. 19, 1974 which is a continuation-in-part application of Ser. No. 401,207 filed by Myron J. Block on Sept. 27, 1973 (now abandoned), and commonly assigned with the present application. The Block technique employs a phenomenon known as multiple attenuated total reflection (ATR).

This ATR phenomenon occurs when a light beam, traveling in a first medium of a given refractive index, impinges upon an interface between the first medium and a second medium having a different index of refraction, at an angle of incidence greater than the critical angle. In such cases, in accordance with Snell's law, so-called total reflection of the beam will occur. Additionally, the incident beam will also set up an inhomogeneous optical surface wave in the second medium. This latter wave, also termed an evanescent or lateral wave, propagates parallel to the reflecting interface and its field strength attenuates exponentially in a direction normal to the interface. If the second medium is non-absorbent, the energy in the evanescent wave eventually returns to the reflected beam in the first medium, thus making the reflection truly total. If the second medium is absorbent, some of the evanescent wave energy will be absorbed and the reflection is not truly total. The same phenomenon arises with light traversing a waveguide or light guide such as a film of light transmissive material having a thickness around the order of the wavelength of light. For purposes herein, any system in which this ATR phenomenon arises when light traverses therethrough will be generally referred to as a "totally internally reflecting cell." ATR has since been widely used in analytical systems, as described in N. J. Harrick, "Internal Reflection Spectroscopy," New York, Interscience, 1967. ATR in light guides and systems for coupling such light guides to light sources are described by P. K. Ten in "Light Waves in Thin Films and Integrated Optics," *Applied Optics*, November 1971 pp. 2395–2413.

In accordance with the Block technique, a sample is initially prepared to limit the population to the desired particles. Thus, for example, a biological fluid sample is stained with a fluorescent stain which selectively coupled to all nucleic acid-containing particles and molecules. The resulting stained particles will include whole cells, mitochondriae, chromosomes, ribosomes, messenger and transfer RNA as well as viruses. The first three, being much larger in size than even the largest viruses, may be efficiently rejected by filtering the sample through a Millipore filter; the last two, much smaller in molecular weight than the smallest viruses, can be wholly eliminated by rapid dialysis in a hollow fiber. Thus, there is provided a sample in which the only fluorescent particles are the viruses, ribosomes, the very largest messenger RNA and some fragments of larger particles.

This sample is placed to provide an interface with a totally internally reflecting cell and exciting radiation directed into one end of the cell, creating an excited zone or region in the sample. As Brownian motion causes the particles to drift through this region or field of view (which can be referred to as the ATR "aperture") substantially complete modulation of particle emission takes place over a few hundred A of travel. The sharpness of the boundary of the region is such that modulation frequencies, derived by autocorrelation of the outwardly random noise in the signal, go from 0 to 1 kHz for the 180–3500 A virus size range.

By computing, in appropriate instrument circuitry, the log-log fast Fourier transform of the autocorrelation curve of the signal-averaged AC component of the fluorescent signal, one obtains a straight line graph the slope of which is proportional to the particle hydrodynamic radius, and the intercept of which is proportional to the product of the particle concentration times the particle nucleic acid content.

As disclosed in the Block application, the modulation of intensity provided by each particle as it moves in or out of the ATR aperture is a function which is at least in part dependent on the amplitude of the fluorescent emission from the particle. Because a given species of particles is to be identified by the identification of its characteristic function through Fourier analysis, it is quite apparent that it is highly desirable to provide, across the entire field of view or aperture of the system into and out of which particles will move by Brownian motion, distribution as uniform as possible of exciting radiation intensity.

Ordinarily, absorption either in the transmitting medium or scattering by particulate matter encountered, will attenuate both a beam of radiation traversing a totally internally reflecting cell and the evanescent wave associated with the beam. Such attenuation results in a non-uniform distribution of intensity of the evanescent wave in the ATR aperture with a resulting undesirable, position dependent variation in the amplitude of fluorescent emission from identical particles. Such positional variation in emission amplitude tends to degrade the precision of a Fourier analysis, particularly where the sample contains a very low concentration of the desired particle population. To avoid such an effect, one can of course limit the lateral dimension of the aperture to a very small size so that the intensity distribution does not markedly vary depending on the position within the apertuure, but such size limitation is undesirable because it reduces sampling frequency.

A principal object of the present invention is therefore to obviate a number of the problems above delineated, and particularly to provide a system which will furnish a relatively more uniform illumination between the points at which exciting radiation enters a cell and the points at which it leaves.

Another object of the present invention is to provide an improved system of the type described in which a greater illuminated area can be made use of for analysis purposes.

Yet another object of the present invention is to provide an improved system of the type described which allows for a variable penetration angle of the exciting radiation into the cell by simple translation of one or more of the various elements of the system along the optical axis of the system.

Still another object of the present invention is to provide an improved apparatus for accurately detecting submicron-dimensioned particles by Fourier analysis with a greater illuminated area.

These and other objects are achieved by a system which comprises a totally internally reflecting cell, means for providing radiation of at least one selected wavelength, means for directing the radiation along a plurality of paths, and means for introducing the radiation of at least two of the paths into first and second opposite portions of the cell so that the level of illumination in the cell is approximately equalized at all points between the opposed portions. Means are also provided for varying the penetration angle of the exciting radiation into the cell.

Other objects of the invention will in part be obvious and will in part appear hereinafter. The invention accordingly comprises the apparatus possessing the construction, combination of elements, and arrangement of parts, all of which are exemplified in the following detailed disclosure and the scope of the application of which will be indicated in the claims.

For a fuller understanding of the nature and objects of the present invention, reference should be had to the following detailed description taken in connection with the accompanying drawings wherein:

FIG. 1 is a partly schematic side view of the preferred embodiment of the present invention;

FIG. 2 is a partly schematic cross-sectional view of the sample holder of the FIG. 1 embodiment;

FIG. 3 is a partly schematic cross-sectional side view of a alternative embodiment of the sample holder;

FIG. 4 is a partly schematic side view of an alternative embodiment of the present invention;

FIG. 5 is a schematic top view of the illuminated area of the cell of the FIG. 1 embodiment; and FIG. 6 is a schematic top view of the illuminated area of the cell of the FIG. 4 embodiment.

In the drawings, like numerals refer to like parts.

Referring now to FIG. 1 of the drawings, there is shown the preferred device embodying the principles of the present invention and comprising sample holder 22 which is intended to be illuminated by illumination system 20 and observed by observation system 24.

Illumination system 20 of the present invention preferably includes source 26 which provides beam 28 of radiation. The latter typically includes radiation of a selected one or a narrow band of wavelengths. While the present invention does not depend upon Doppler shifting and in that respect coherent illumination is not required, it may be desirable to provide exciting beam 28 in a comparatively narrow band of wavelengths, which differs substantially from the wavelenghts of the excited fluorescent emission. Hence, source 26 may be typically a monochromator and a spectral filter 30 is provided for selecting the desired wavelengths. Preferably source 26 is a laser to provide a high intensity monochromatic beam, a particularly desirable feature in view of the minuteness of the particles being sought. As will be evident hereinafter, the spatially and temporally coherent aspects of a laser beam can be used to create an interference pattern which can serve as a spatial filter useful in providing intensity modulation of fluorescing particles. Source 26 may include means (not shown) for collimating output beam 28 (in the event source 26 is not a laser) which is also a desirable feature to maintain total reflection.

"Axicon" 32, i.e. a conical refractive element is disposed with its axis of revolution parallel to beam 28 and its apex directed toward source 26. When a collimated, substantially monochromatic beam of light (the word "light" as used herein denoting the ultraviolet, visible and infrared portion of the electromagnetic spectrum) impinges on the apex of axicon 32, the light is refracted by the axicon along a plurality of paths of equal intensity to form a divergent beam 34 which is a conical annulus.

Condenser 36 is positioned in beam 34 so that the latter is preferably refracted into a converging annular beam 38. Although condenser 36 is shown as a simple meniscus lens, it should be appreciated that the condenser may comprise other types of lenses or combination of lenses, or reflecting elements which will refract or reflect a diverging annular beam of light into a converging annular beam of light. Disposed in the path of beam 38 is member 40, preferably an annular specularly reflecting mirror which has an inner frusto-conical surface 41. Surface 41 is positioned so that it can direct at least parts of beam 38 into totally internally reflecting cell 44 comprising a portion of sample holder 22.

Sample holder 22 is shown in greater detail in FIG. 2 as comprising cell 44 which is preferably an optically thin waveguide film supported on transparent slab 42. Of course, cell 44 may take other forms such as a plate or the like. As a condition for obtaining an evanescent wave at an interface of interest, cell 44 must provide an optical path through material having a greater refractive index than the refractive index of the medium bounding the other side of that interface of interest. The refractive index of the cell 44 must also be greater than the refractive index of the slab 42 in order to provide total internal reflection through the film. The material of cell 44 must also be transparent over the wavelength range of the exciting beam of radiation and should possess appropriate physical and chemical stability with respect to both the exciting radiation and the medium, typically a fluid, used to form an interface with the cell. Among the typical materials which may be used for cell 44 are various single-crystal films; glasses such as crown glass and frit glass, quartz fused silica; synthetic organic polymers such as polystyrene, polymethacrylate or polyurethane, and the like.

Cell 44 is deposited or secured to upper surface 46 of slab 42 to form a first interface therebetween. While slab 42 and cell 44 can assume a number of configurations, as shown in FIG. 2, preferably both are circular, flat sheets or material. The largest opposed sides or surfaces 48 and 50 of cell 44 are substantially parallel with one another, surface 48 being in contact with surface 46 of slab 42. Optimally, surfaces 48 and 50 of the cell are optically plane so as to minimize the amount of light leakage therethrough due to minute imperfections which might cause the angle of incidence of a reflecting beam to exceed the critical angle at the imperfection. Typically, the slide 42 will approximate a 2.5 cm diameter silica microscope slide of about 1 mm thickness. Cell 44 can approximate a 2.5 cm diameter layer, the thickness of which will roughly depend on the wavelength band of beam 38.

In order to direct beam 38 from member 40 into the cell at the critical angle necessary for total internal reflection, holder 22 further includes coupling means 52. Preferably, coupling means 52 is an annular prism which has a triangular cross-section, diagonal surface 54 of which faces reflective surface 41 of member 40. In the preferred embodiment of FIGS. 1 and 2 prism 52 is secured to lower surface 47 of the slab 42. With this arrangement, beam 38 will reflect from the surface 41 through coupling means 52 through slab 42 and into cell 44. Since no means need be provided for decoupling the radiation from cell 44, the radiation will ultimately disperse through opposite edges of the cell. Accordingly, means such as light traps (not shown) may be provided to trap the exciting radiation as it exits the cell so that it is not reflected into the observation system 24.

In an alternative embodiment, illustrated in FIG. 3, coupling means 52 is shown as being secured directly to surface 50 of cell 44. With this arrangement beam 38 will reflect from surface 41 directly to coupling means 52 and then into cell 44.

Coupling means 52 may be secured to slab 42 or cell 44 as the case may be, in any optically suitable manner and is preferably cemented with an appropriate optical cement of the proper index of refraction.

In order to receive and retain a fluid sample to form a desired interface with cell 44, holder 22 of both the embodiments of FIGS. 2 and 3, further comprises cover plate 58, positioned over and spaced from cell 44 by spacer 56 to provide a volume or well 60. Spacer 56 is preferably a circular ring made of a material of a refractive index which is substantially less than the refractive index of the cell. Spacer 56 is secured to the cell surface by any suitable process such as cementing the ring thereto with an optical cement. Cover plate 58 is made of a material which is transparent to the fluorescent radiation emitted by the particles in the fluid sample held in well 60 and moving in the evanescent wave created by beam 38.

The distance that an evanescent or lateral wave penetrates effectively into the fluid medium in well 60 can be varied between a minimum as small as 1/20 of a wavelength and a maximum of several wavelengths, by changing the angle of incidence of the internally multiply reflected beam within cell 44 particularly close to the critical angle. This can be accomplished by providing means such as a rack and pinion arrangement (not shown) for moving one or both of axicon 32 and condenser 36 with respect to one another along their optical axes. Such movement will result in a change in the angle of convergence of beam 38 exiting and thus vary the angle at which beam 38 enters surfaces 48 or 50 of the cell 44 as the case may be. As previously noted, it is desirable that beam 38 be both monochromatic and collimated. Thus, if such radiation is used it will be appreciated that one can tune cell 44 with respect to the effective depth of the evanescent wave by introducing the beam 38 into coupling means 52 at variable angles without regard to any chromatic aberrations.

In an alternative embodiment, illustrated schematically in FIG. 4, the conical axicon 32 is replaced with a triangularprismatic element 32a, condenser 36 is replaced with a cylindrical lens 36a, annular member 40 is replaced with two flat reflective elements 40a and 40b, and coupling prism 52 is replaced with a pair of triangular prisms 52a and 52b. In such case, only two input edges are needed for cell 44, both edges preferably being plane. Hence cell 44 is the embodiment of FIG. 4 can be rectangular. Prism 32a is positioned so that beam 28 impinges on the apex being thereby refracted into two substantially planar beams 34a and 34b of equal intensity. Each beam is refracted by cylindrical lens 36a to the pair of reflective members 40a and 40b, respectively where each is coupled into the cell 44 by triangular coupling prisms 52a and 52b, respectively.

The system 24 for observing fluorescent emissions from a sample in well 60 can be any type of system for observing or detecting the excited region. Preferably, system 24 is of the type described in my copending application Ser. No. 375,807 filed July 2, 1973 which can be employed to achieve size discrimination. Generally, system 24 comprises an optical system which includes objective lens means which may include one or more optical elements, e.g. refractive and reflective as well known in the art. System 24 may also include means (not shown) for focusing the objective lens means 62 on the particles moving in the excited region or the system may be a fixed focus system. Thus, the first conjugate plane (i.e. object plane) of system 24 is or can be made substantially coplanar with the excited region or ATR aperture in well 60 traversed by an evanescent wave formed responsively to passage of exciting beam 38 through cell 44 by multiple total reflection.

The preferred embodiment also includes spectral filter 64 which serves to limit the effective spectral bands seen by the detector 68 so that the system 24 can discriminate among different fuorescence bands arising from particles which have affinities for different dyes. For example, it is known that viruses consist essentially of either deoxyribonucleic acid or ribonucleic acid, usually surrounded by a protein shell, and that such nucleic acids can be dyed by certain unique dyes each providing a characteristic fluorescent emission spectrum quite distinct from one another.

Observation of intensity modulation of the fluorescing particles serves to distinguish viral-like particles from background and provides useful viral classification descriptors. A spatial filter (not shown) accordingly can be imaged in the plane of the sample which is placed in well 60. The spatial filter may precede the holder 22 (for example it can be positioned in beam 38) or the holder may precede the spatial filter in the light path. In the latter case, the sample is typically imaged onto the filter by objective 62. Spatial filters are well known to those skilled in the optical arts and may be a single aperture or multiaperture filter and may take the form of gratings, grids, annuli and the like. Each defines one or more edges between a relatively light-transmitting element and a relatively non-transmitting element. It will be apparent that as a particle moved by Brownian forces, or its image crosses the edge of the spatial filter to a light-transmitting area, the detector 68 will see that particle somewhat as a light burst or scintillation. As the particle crosses the edge into a non-transmitting area, the burst is extinguished. Thus, assuming that a particle travels in a straight line across a grid, the observed intensity of emission from the particle will fluctuate between maximum and minimum values at a frequency depending on the grid spacing and the particle velocity. Theoretically, for optimum modulation and duty cycle, the grid spacing should, at least in order of magnitude, match the particle size. The ATR "aperture" provided by one present invention can be so matched. And, as noted previously, where source 26 is a laser, the spatially coherent beam 28 will be refracted by the axicon 32 and condenser 38 along a plurality of paths where it will be coupled into the cell 44. Since radiation is coupled into opposite points of the cell and reflected toward each other, the spatial and temporal coherency of the beam may provide interference patterns resulting in lighter and darker zones. Such zones will themselves divide the ATR aperture as a second orthogonal spatial filter thereby providing another order of modulation.

In operation in the embodiments of FIGS. 1–3, monochromatic beam 28 provided by light from source 26 and filter 30 impinges upon the apex of axicon 32, whereupon beam 28 is refracted to form beam 34. Beam 34 is directed by condenser 36 onto the annular reflecting member 40 which rejects annular beam 38 toward the annular coupling prism 52. Beam 38 is thus introduced into cell 44 at an angle greater than the critical angle so as to achieve multiple total internal reflection therethrough. As illustrated in FIG. 5, it will be appreciated that since beam 38 of the preferred embodiment is annular and is coupled to an annular prism, the beam enters cell 44 around the entire perimeter defined or prescribed by the prism. The beam is internally reflected through the cell from every point on the perimeter of the prism, through the center, to the diametrically opposite side of the prism where it can be decoupled from the cell. Thus, as the portion of the beam 38 entering at point A on the perimeter is internally reflected from point A to the diametrically opposite point B it will be attenuated because of absorption, scattering and the like. If this attenuation of the illumination is the reverse of the attenuation of the illumination as the beam passes from point B to point A, the sum of the two beams at all points between A and B is substantially a constant.

Similar results occur in the FIG. 4 embodiment as illustrated in FIG. 6.

As the evanescent wave produced by the beam 38 propagates parallel to top surface 50 of cell 44 and is exponentially attenuated in the medium in well 60 from the interface between the medium and top surface. The Brownian motion of small particles will move the particles in and out of that layer region in the medium in which the evanescent wave has a substantial field intensity causing radiant emission, either through scattering of the evanescent wave by the moving particles or by fluorescence excited in the particles by the evanescent wave. The emission from particles will be modulated, i.e. appear to scintillate, the scintillation duration being established by the length of time that the particle remain in the excited region within the medium. Particles outside of the excited region will of course not emit appropriate radiation and hence will not be visible.

The radiation emitted by the excited particles in the sample passes through the filter 64 through field stop 66, whereupon it impinges on the detector 68. Stop 66 is well known in the art and generally used simply to determine or limit the extent of the object or field that will be seen by the detector 68. Detector 68 may be any type of known spectrally responsive as well as intensity responsive detector, and is preferably a photomultiplier tube well known in the art. The electrical output signals from the detector 68 can be amplified and applied to a known frequency analyzer (not shown). The frequency analyzer output can be applied to data reduction apparatus (not shown) which may be a strip chart recorder and/or a computer.

Since certain changes may be made in the above apparatus without departing from the scope of the invention herein involved, it is intended that all matter contained in the above description or shown in the accompany drawing shall be interpreted in an illustrative and not in a limiting sense.

What is claimed is:

1. In a system having a totally internally reflecting cell and a source of a beam of radiation of at least one selected wavelength, the improvement comprising:
   means for directing said radiation along a plurality of paths; and
   means for introducing the radiation in at least two of said paths into first and second opposite portions of said cell whereby the level of illumination in said cell is approximately equalized at all points between said opposed portions.

2. The system in accordance with claim 1, wherein said directing means includes an axicon having its apex directed toward said source so as to refract said beam into a conical annular beam.

3. The system in accordance with claim 1, wherein said directing means includes a prism having its apex directed toward said source so as to split said beam along two of said paths.

4. The system in accordance with claim 2, further including means for varying the conical angle of said conical angular beam.

5. The system in accordance with claim 4, wherein said means for varying the angle includes a condenser positioned between said axicon and said means for introducing, at least one of said condenser and said axicon being movable with respect to the other so as to change said conical angle of said conical annular beam.

6. The system in accordance with claim 1, wherein said means for introducing includes at least one prism.

7. The system in accordance with claim 6, wherein said prism is torodial and has a triangular cross-section.

8. The system in accordance with claim 1, wherein said means for introducing includes a pair of elongate prismatic elements, each of said prismatic elements having a triangular cross-section.

9. The system in accordance with claim 8 further including means for reflecting radiation, spaced from said prismatic elements so as to reflect radiation to said prismatic elements from said means for directing.

10. The system in acordance with claim 1, wherein the radiation in said at least two paths is spatially and temporally coherent.

11. Apparatus in accordance with claim 10, wherein said variable penetration angle means includes a condenser optically positioned between said means for directing said radiation and said means for introducing said radiation, said condenser and directing means being movable with respect to one another so as to change the direction of said at least two paths.

12. Apparatus for detecting submicron dimensional particles in a fluid medium, said apparatus comprising, in combination:
   means for providing radiation of at least one selected wavelength;
   a totally internally reflecting cell bounded at least in part by an interface with said medium;
   means for directing said radiation along a plurality of paths;
   means for introducing said radiation in at least two of said paths into first and second opposite portions of said cell whereby the level of illumination in said cell is approximately equalized at all points between said opposed portions; and
   imaging optical means for observing said particles in a first conjugate plane substantially coincident with the region of said medium traversed by an evanexcent wave formed upon internal reflection of said radiation of said at least two paths of radiation within said cell.

13. Apparatus in accordance with claim 12 wherein said directing means includes means for forming an annular beam of said radiation.

14. Apparatus in accordance with claim 12 further including means for varying the angle of introduction of said radiation of said at least two paths into said cell so as to vary the penetration of said evanescent wave.

* * * * *

UNITED STATES PATENT OFFICE
CERTIFICATE OF CORRECTION

PATENT NO. : 3,999,855
DATED : December 28, 1976
INVENTOR(S) : Tomas Hirschfeld

It is certified that error appears in the above-identified patent and that said Letters Patent are hereby corrected as shown below:

Claim 4, line 21 (Column 8) "angular" should read --annular--;

Claim 12, line 65 (Column 8) "evanexcent" should read --evanescent--.

Signed and Sealed this

Twenty-second Day of March 1977

[SEAL]

Attest:

RUTH C. MASON
*Attesting Officer*

C. MARSHALL DANN
*Commissioner of Patents and Trademarks*